United States Patent
Geret et al.

(10) Patent No.: US 11,140,896 B2
(45) Date of Patent: Oct. 12, 2021

(54) TWO COMPONENTS DISINFECTING COMPOSITION CONTAINING PERACETIC ACID AND CHELATING AGENT

(71) Applicant: ECOLAB USA INC., Saint Paul, MN (US)

(72) Inventors: Laurence Geret, Pulheim (DE); Michael Decker, Solingen (DE); Stefan Jäger, Ingelheim (DE)

(73) Assignee: Ecolab USA Inc., Saint Paul, MN (US)

( * ) Notice: Subject to any disclaimer, the term of this patent is extended or adjusted under 35 U.S.C. 154(b) by 0 days.

(21) Appl. No.: 16/801,607

(22) Filed: Feb. 26, 2020

(65) Prior Publication Data

US 2020/0187496 A1  Jun. 18, 2020

Related U.S. Application Data

(63) Continuation of application No. 15/529,170, filed as application No. PCT/EP2014/076007 on Nov. 28, 2014, now Pat. No. 10,609,925.

(51) Int. Cl.
| | | |
|---|---|---|
| *A01N 25/22* | (2006.01) | |
| *A61L 2/18* | (2006.01) | |
| *A01N 57/20* | (2006.01) | |
| *A01N 25/02* | (2006.01) | |
| *A01N 59/00* | (2006.01) | |
| *A01N 37/16* | (2006.01) | |
| *A01N 37/02* | (2006.01) | |

(52) U.S. Cl.
CPC .............. *A01N 25/22* (2013.01); *A01N 25/02* (2013.01); *A01N 37/02* (2013.01); *A01N 37/16* (2013.01); *A01N 57/20* (2013.01); *A01N 59/00* (2013.01); *A61L 2/18* (2013.01); *A61L 2202/24* (2013.01)

(58) Field of Classification Search
CPC ................................ A01N 59/00; A01N 25/22
See application file for complete search history.

(56) References Cited

U.S. PATENT DOCUMENTS

| 4,051,058 | A | 9/1977 | Böwing et al. |
| 4,304,762 | A | 12/1981 | Leigh |
| 6,257,253 | B1 | 7/2001 | Lentsch et al. |
| 6,527,872 | B1 | 3/2003 | Fricker et al. |
| 2002/0004057 | A1 | 1/2002 | Tabasso |
| 2005/0054545 | A1 | 3/2005 | Biering et al. |
| 2011/0195481 | A1 | 8/2011 | Svendsen et al. |
| 2012/0172441 | A1 | 7/2012 | Li et al. |
| 2013/0247308 | A1 | 9/2013 | Duerrschmidt et al. |

FOREIGN PATENT DOCUMENTS

| CN | 102827016 A | 12/2012 |
| EP | 0357238 B1 | 7/1999 |
| EP | 1123655 B1 | 8/2001 |
| EP | 1293215 A1 | 3/2003 |
| JP | 5332679 B2 | 11/2013 |
| WO | 2006015626 A1 | 2/2006 |
| WO | 2010011746 A2 | 1/2010 |
| WO | 2012054391 A2 | 4/2012 |

OTHER PUBLICATIONS

Ecolab Inc., PCT/EP2014/076007 filed Nov. 28, 2014, "The International Search Report and the Written Opinion of the International Searching Authority, or the Declaration," dated Mar. 20, 2015.

"Deionized/Demineralized Water", https://www.lenntech.com/applications/process/demineralised/deionised-demineralised-water.htm#ixzz6nri5eNkA, 6 pages, Jan. 3, 2021.

Malchesky, Paul S., "Medical Applications of Peracetic Acid", Disinfection, Sterilization, and Preservation, Ch. 49, pp. 979-996, 2001.

Mücke, von H., "Über die Eigenschaften der Peressigsäure" Wissenschaftliche Zeitschrift der Universität Restock, 4 pages, 1970.

Pinto et al., "Biodegradable chelating agents for industrial, domestic, and agricultural applications—a review", vol. 21, pp. 11893-11906, 2014.

Pinto et al., "Pre-treatment of the paper pulp in the bleaching process using biodegradable chelating agents, Int. J. Environ. Sci. Technol.", vol. 12, pp. 975-982, 2015.

Ein Service des Bundesministeriums der Justiz und für Verbraucherschutz sowie des Bundesamts für Justiz, "Verordnung über die Qualität von Wasser für den menschlichen Gebrauch (Trinkwasserverordnung—TrinkwV)", https://www.gesetze-im-internet.de/trinkwv_2001/8JNR095910001.html, 45 pages, May 21, 2001.

*Primary Examiner* — Kyle A Purdy
(74) *Attorney, Agent, or Firm* — McKee, Voorhees & Sease, PLC

(57) ABSTRACT

The invention relates to a disinfectant composition comprising:
(A) a peracetic acid-generating component comprising acetic acid, hydrogen peroxide and an organic phosphonic acid; and
(B) a stabilizer component comprising an alkaline agent and a chelating agent,
wherein the chelating agent is selected from the group consisting of N,N-bis(carboxymethyl)L-glutamic acid, methylglycine diacetic acid, nitrilotriacetic acid, and alkali metal salts thereof, and a mixture of two or more thereof and to the aqueous disinfectant solution obtainable by mixing and diluting components (A) and (B) in water.

The invention further relates to a method of disinfecting surface and instruments, particularly flexible endoscopes, using said aqueous disinfectant solution.

13 Claims, No Drawings

TWO COMPONENTS DISINFECTING COMPOSITION CONTAINING PERACETIC ACID AND CHELATING AGENT

CROSS-REFERENCE TO RELATED APPLICATIONS

This is a Continuation Application of U.S. Ser. No. 15/529,170, filed May 24, 2017, which is a National Phase Application claiming priority to PCT/EP2014/076007, filed Nov. 28, 2014, all of which are herein incorporated by reference in their entirety.

FIELD OF THE INVENTION

The invention relates to a disinfectant composition, especially for the disinfection of medical instruments, and to a method for the disinfection of surfaces, especially for the disinfection of medical instruments.

BACKGROUND

The effective disinfection of surfaces, particularly of contaminated instruments is an important requirement in the medical field, and medical instruments that are exposed to blood or other body fluids require disinfection between each use. The disinfection of delicate instruments such as flexible endoscopes, which are used in medical diagnosis and therapy and in surgical operations, still is performed to a significant extent manually using liquid disinfectants.

Numerous aqueous compositions containing a wide variety of disinfecting ingredients for the chemical disinfection of instruments are available. Preparations based on aldehydes have been widely used in practice, and also preparations based on peroxidic active ingredients, more particularly peracetic acid, are used for this application. Document US 2011/0217204 A1 describes a composition, comprising an anti-microbial agent comprising peracetic acid, and a reagent mixture comprising a buffer, an anticorrosive agent and a chelator, which can be ethylenediaminetetraacetic acid, hydroxyethylidenediphosphonic acid or sodium salts thereof.

However, particularly the shelf life of the use-solution of peroxidic systems still may be improved.

Therefore, the object underlying the present invention was to provide a disinfectant composition providing an improved shelf life.

SUMMARY

It is provided a disinfectant composition comprising:
(A) a peracetic acid-generating component comprising acetic acid, hydrogen peroxide and an organic phosphonic acid; and
(B) a stabilizer component comprising an alkaline agent and a chelating agent,
wherein the chelating agent is selected from the group consisting of N,N-bis(carboxymethyl)L-glutamic acid, methylglycine diacetic acid, nitrilotriacetic acid, and alkali metal salts thereof, and a mixture of two or more thereof.

It has been surprisingly found that the peracetic acid in a use solution obtained by mixing the components (A) and (B) with an appropriate amount of water could be stabilised up to 7 days or more when the chelating agent in the component (B) was selected from N,N-bis(carboxymethyl)-L-glutamic acid, methylglycine diacetic acid, nitrilotriacetic acid or an alkali metal salt of these acids. It is provided the advantage of a particular superior stabilisation of peracetic acid by using N,N-bis(carboxymethyl)-L-glutamic acid tetrasodium salt (GLDA), methylglycine diacetic acid (MGDA) or trisodium nitrilotriacetate (NTA) at a concentration level of 0.1 wt.-% in the component (B) compared to tripolyphosphate, ethylenediaminetetraacetic acid (EDTA) or phosphonate.

In accordance with another aspect is provided an aqueous disinfectant solution obtainable by diluting the disinfectant composition in water.

Advantageously can be provided an aqueous disinfectant solution providing a shelf life which was prolonged to more than 7 days, and at a concentration level of 0.1 wt.-% of the chelating agent in the component (B) even up to 14 days before the level of peracetic acid in the use solution falls below a level of 1000 ppm. The aqueous disinfectant solution is suitable for disinfecting surfaces, particularly instruments such as medical or surgical instruments, particularly for the manual disinfection of flexible endoscopes.

Further is provided a method of preparing an aqueous disinfectant solution by diluting the disinfectant composition in water.

In accordance with another aspect is provided a method for disinfecting a surface, particularly an instrument such as a medical or surgical instrument, comprising the steps of providing an aqueous disinfectant solution, and contacting the surface with the aqueous disinfectant solution for an effective period of time to disinfect the surface.

Definitions

The term "disinfection" as used herein means an inactivation or reduction of microorganisms on a surface to which the disinfectant solution is applied. In some embodiments, the term "disinfection" may refer to the disinfection of medical devices, particularly according to the European medical devices directive (MDD) 93/42/EEC.

The term "two-component composition" refers to a composition that comprises two components, e.g. a peracetic acid-generating component comprising the precursors acetic acid and hydrogen peroxide, and a stabilizer component. The two components can be mixed with an appropriate amount of solvent before use to form a use solution.

The term "aqueous" solution refers to a solution in which the solvent is water. An aqueous disinfectant solution refers to a disinfectant solution in which the solvent is water.

The term "chelating agent" refers to a compound or molecule, which is capable of coordinating or binding metal ions commonly found in natural water such as calcium, magnesium, iron and manganese metal ions.

The term "alkaline agent" refers to a compound or molecule, which is capable of modulating the pH value of a solution by providing a source of alkalinity.

As used herein the term "peracetic acid-generating component" refers to a composition that generates peracetic acid when the ingredients or substances of the component, particularly acetic acid and hydrogen peroxide, are combined. Peracetic acid is formed as an equilibrium product from acetic acid and hydrogen peroxide.

As used herein the term "stabilizer component" refers to a composition that stabilizes the peractic acid at a neutral pH when added to an aqueous solution containing the peracetic acidgenerating component. The stabilizer component advantageously can shift the corrosive pH of a solution comprising the pearacetic acid-generating component to a more material compatible pH value. The stabilizer component (B), when added to an aqueous solution containing a peracetic acid-generating component (A) can stabilize the peractic acid at a neutral pH significantly more compared to solutions that do not contain the stabilizer component.

Weight percent, weight-% or wt.-% are synonyms that refer to the concentration of a substance as the weight of the substance divided by the weight of the composition and multiplied by 100. The weight-% (wt.-%) of the components are calculated based on the total weight amount of the composition, if not otherwise stated.

The total amount of all components of the composition does not exceed 100 wt.-%. The remainder up to 100 wt.-% of the composition can be water. The water content of the composition is simply determined by subtracting the amounts of all the other ingredients from 100 wt.-%.

The term "ppm" meaning one part per million as used herein refers to a quantity-per-quantity measure denoting one part per 1,000,000 parts or one part in $10^6$, e.g. referring to the concentration of a substance based on the total weight of a solution 1000 ppm means 0.1 wt. %.

All numeric values are herein assumed to be modified by the term "about", whether or not explicitly indicated. As used herein, the term "about" refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

It should be noted that, as used in this specification and the appended claims, the singular forms "a", "an" and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

DETAILED DESCRIPTION

Surprisingly it has been discovered that the disinfectant composition comprising:
(A) a peracetic acid-generating component comprising acetic acid, hydrogen peroxide and an organic phosphonic acid; and
(B) a stabilizer component comprising an alkaline agent and a chelating agent,
wherein the chelating agent is selected from the group consisting of N,N-bis(carboxymethyl)L-glutamic acid, methylglycine diacetic acid, nitrilotriacetic acid, and alkali metal salts thereof, and a mixture of two or more thereof, provides a use solution obtained by mixing the components (A) and (B) with an appropriate amount of water with an improved stabilisation of peracetic acid of 7 days or more.

In an embodiment, the disinfectant composition may be a two-component disinfectant composition comprising:
(A) a peracetic acid-generating component comprising acetic acid, hydrogen peroxide and an organic phosphonic acid; and
(B) a stabilizer component comprising an alkaline agent and a chelating agent,
wherein the chelating agent is selected from the group consisting of N,N-bis(carboxymethyl)L-glutamic acid, methylglycine diacetic acid, nitrilotriacetic acid, and alkali metal salts thereof, and a mixture of two or more thereof.

The stabilizer component (B) comprises an alkaline agent and a chelating agent. It was found that a chelating agent selected from the group consisting of N,N-bis(carboxymethyl)-L-glutamic acid, methylglycine diacetic acid, nitrilotriacetic acid, an alkali metal salt of these acids, or a mixture of two or more thereof considerably can improve the shelf life of a use solution.

The peracetic acid-generating component (A) and the stabilizer component (B) can be prepared by mixing the respective ingredients or substances of the components with an appropriate amount of water. The components (A) and (B) are aqueous compositions, and water is added ad 100 wt.-% as the solvent.

According to one embodiment, the stabilizer component (B) comprises from equal or more than about 0.05 wt.-% to equal or less than about 3 wt.-%, preferably from equal or more than about 0.05 wt.-% to equal or less than about 1 wt.-%, more preferably from equal or more than about 0.1 wt.-% to equal or less than about 0.5 wt.-%, based on the total weight of the stabilizer component (B), of the chelating agent. Such amounts of the chelating agent in the stabilizer component (B) provide very good and lasting level of peracetic acid. Particularly, an amount from equal or more than about 0.1 wt.-% to equal or less than about 0.5 wt.-% of the chelating agent was able to stabilise a use solution obtained by mixing the components (A) and (B) with the appropriate amount of water for up to 14 days before the level of peracetic acid in the use solution falls below a level of 1000 ppm.

The chelating agent may be N,N-bis(carboxymethyl)-L-glutamic acid, methylglycine diacetic acid, nitrilotriacetic acid, or an alkali metal salt of these acids. The alkali metal salt of N,Nbis(carboxymethyl)-L-glutamic acid, methylglycine diacetic acid or nitrilotriacetic acid may be a sodium or a potassium salt. Sodium and potassium salts provide a good solubility. Or, the chelating agent may be a mixture of two or more of N,N-bis(carboxymethyl)-L-glutamic acid, methylglycine diacetic acid, nitrilotriacetic acid or an alkali metal salt particularly a sodium or potassium salt of these acids. A preferred salt of N,N-bis(carboxymethyl)-L-glutamic acid, methylglycine diacetic acid, or nitrilotriacetic acid may be a sodium salt. A preferred sodium salt of N,N-bis(carboxymethyl)-L-glutamic acid is N,N-bis(carboxymethyl)-L-glutamic acid tetrasodium salt. A preferred sodium salt of methylglycine diacetic acid is methyl glycine diacetic acid, trisodium salt, which also is denoted alanine, N,N-bis(carboxymethyl)-, sodium salt (1:3) according to IUPAC nomenclature. A preferred sodium salt of nitrilotriacetic acid is trisodium nitrilotriacetate. Nitrilotriacetic acid also is denoted 2[bis(carboxymethyl)amino]acetic acid according to IUPAC nomenclature.

The chelating agent may be selected from N,N-bis(carboxymethyl)-L-glutamic acid tetrasodium salt, methyl glycine diacetic acid and trisodium nitrilotriacetate. According to an embodiment, the chelating agent is N,N-bis(carboxymethyl)-L-glutamic acid tetrasodium salt. N,N-bis(carboxymethyl)-L-glutamic acid tetrasodium salt also is denoted L-Glutamic acid, N,N-bis(carboxymethyl)-, sodium salt (1:4) according to IUPAC nomenclature, or is denoted glutamic acid-N,N-diacetic acid. According to another embodiment, the chelating agent is methyl glycine diacetic acid. According to another embodiment, the chelating agent is trisodium nitrilotriacetate.

The stabilizer component (B) also comprises an alkaline agent. The alkaline agent can modulate the pH value by providing a source of alkalinity. According to an embodiment, the alkaline agent is selected from the group consisting of sodium hydroxide, potassium hydroxide, monoethanolamine, diethanolamine, triethanolamine, ammonia, ammonium hydroxide and mixtures thereof.

The alkaline agent may be a hydroxide selected from the group consisting of sodium hydroxide (NaOH) and potassium hydroxide (KOH), preferably sodium hydroxide. Sodium hydroxide and potassium hydroxide both are good alkalis. In industrial scale, sodium hydroxide is more widely used than potassium hydroxide. Further, sodium hydroxide is typically a purer chemical than potassium hydroxide. Sodium hydroxide and potassium hydroxide industrially are available in multiple fluid and solid form. Alternatively, the alkaline agent may be an ethanolamine selected from the group consisting of monoethanolamine, diethanolamine and triethanolamine. Alternatively, the alkaline agent may be ammonia or ammonium hydroxide.

According to embodiments, the stabilizer component (B) comprises from equal or more than about 3 wt.-% to equal or less than about 10 wt.-%, preferably from equal or more than about 4 wt.-% to equal or less than about 6 wt.-%, more preferably from equal or more than about 4.9 wt.-% to equal or less than about 5.5 wt.-%, based on the total weight of the stabilizer component (B), of the alkaline agent. Such amounts of alkaline agent in the stabilizer component (B) can provide for a pH value of the use or aqueous disinfectant solution in the range from about 3 to 7.

According to one embodiment, the stabilizer component (B) comprises, based on the total weight of the stabilizer component (B), about 0.1 wt.-% or about 0.5 wt.-% N,N-bis(carboxymethyl)-L-glutamic acid tetrasodium salt and about 4.95 wt.-% sodium hydroxide, and water ad 100 wt.-%. According to another embodiment, the stabilizer component (B) comprises, based on the total weight of the stabilizer component (B), about 0.1 wt.-% or about 0.5 wt.-% methyl glycine diacetic acid and about 4.95 wt.-% sodium hydroxide, and water ad 100 wt.-%. According to another embodiment, the stabilizer component (B) comprises, based on the total weight of the stabilizer component (B), about 0.1 wt.-% or about 0.5 wt.-% trisodium nitrilotriacetate and about 4.95 wt.-% sodium hydroxide, and water ad 100 wt.-%.

The peracetic acid-generating component (A) comprises acetic acid and hydrogen peroxide, which form peracetic acid as an equilibrium product. Acetic acid and hydrogen peroxide can function as precursors for generating peracetic acid. The peracetic acid provides the disinfecting efficacy of the use solution. Peracetic acid is fully biodegradable, and hence the disinfecting solution is safe for the environment. The peracetic acid-generating component (A) also comprises an organic phosphonic acid that can improve the stability of the peracetic acid.

In embodiments, the peracetic acid-generating component (A) comprises from equal or more than about 5 wt.-% to equal or less than about 20 wt.-%, preferably from equal or more than about 8 wt.-% to equal or less than about 15 wt.-%, more preferably from equal or more than about 10 wt.-% to equal or less than about 11 wt.-%, based on the total weight of the peracetic acid-generating component (A), of acetic acid.

According to embodiments, the peracetic acid-generating component (A) comprises from equal or more than about 20 wt.-% to equal or less than about 40 wt.-%, preferably from equal or more than about 25 wt.-% to equal or less than about 35 wt.-%, more preferably from equal or more than about 27 wt.-% to equal or less than about 29 wt.-%, based on the total weight of the peracetic acid-generating component (A), of hydrogen peroxide.

According to one embodiment, the organic phosphonic acid is selected from the group consisting of hydroxyethylidene diphosphonic acid and diethylenetriamine penta(methylene phosphonic acid). Preferably, the organic phosphonic acid is 1-hydroxyethylidene-1,1-diphosphonic acid (HEDP).

According to embodiments, the peracetic acid-generating component (A) comprises, based on the total weight of the peracetic acid-generating component (A), from equal or more than about 0.1 wt.-% to equal or less than about 5 wt.-%, preferably from equal or more than about 0.25 wt.-% to equal or less than about 1 wt.-%, more preferably from equal or more than about 0.5 wt.-% to equal or less than about 0.6 wt.-%, of the organic phosphonic acid.

A solution for use in disinfecting surfaces or instruments can be obtained by mixing the peracetic acid-generating component (A) and the stabilizer component (B) with an appropriate amount of water. Such a use solution can combine disinfection efficacy with material compatibility and safety for the user. On the other hand, a concentrated disinfectant composition reduces the inconvenience of handling and storing large volumes of liquid. Further, the amount of packaging is also significantly reduced.

The invention further relates to an aqueous disinfectant solution obtainable by diluting the disinfectant composition in water. The aqueous disinfectant solution can be easily prepared by dispersing or dissolving the components (A) and (B) of the disinfectant composition in water. The water may be deionised water, tap water, processed tap water, or the like. Preferably, the water may be deionised water. The aqueous disinfectant solution provides the solution for the use for disinfection, a so called "use solution".

According to embodiments, the disinfectant solution has a pH value in the range from equal or more than about 3 to equal or less than about 7, preferably in the range from equal or more than about 4 to equal or less than about 6, more preferably in the range from equal or more than about 5 to equal or less than about 6. Such pH values can ensure that a use of the disinfectant solution for medical instruments is safe for the patient, the reprocessing personnel and the medical instrument itself. Further, the aqueous disinfectant solution is non-irritant and non-sensitising for the user. Advantageously, the aqueous disinfectant solution can combine excellent material compatibility with efficient disinfection. The aqueous disinfectant solution so is suitable for use on sensitive medical apparatus.

According to an embodiment, the aqueous disinfectant solution comprises from equal or more than about 1000 ppm to equal or less than about 3000 ppm, based on the total weight of the disinfectant solution, of peracetic acid, for at least 7 days, preferably for at least 14 days.

Such amounts of peracetic acid can provide for short contact times for effective disinfection. So, the aqueous disinfectant solution can reduce reprocessing times for surfaces, particularly for medical instruments. Advantageously, the peracetic acid can be stabilised in the aqueous disinfectant solution for up to 7 days or more, providing a shelf life even up to 14 days before the level of peracetic acid in the solution falls below a level of 1000 ppm at a concentration level of 0.1 wt.-% in the component (B) of N,N-bis(carboxymethyl)-L-glutamic acid tetrasodium salt, methylglycine diacetic acid or trisodium nitrilotriacetate.

Further provided is a method of preparing an aqueous disinfectant solution, comprising diluting the disinfectant composition in water, preferably by diluting from equal or more than about 3 wt.-% to equal or less than about 6 wt.-% of the component (A) and from equal or more than about 3 wt.-% to equal or less than about 6 wt.-% of the component (B), based on the total weight of the aqueous disinfectant solution, in water.

In another embodiment, from equal or more than about 4 wt.-% to equal or less than about 5 wt.-% of the peracetic acid-generating component (A) and from equal or more than about 4 wt.-% to equal or less than about 5 wt.-% of the stabilizer component (B), based on the total weight of the aqueous disinfectant solution, can be diluted in water to prepare an aqueous disinfectant solution. In a further embodiment, from equal or more than about 4.5 wt.-% to equal or less than about 4.8 wt.-% of the component (A) and from equal or more than about 4.5 wt.-% to equal or less than about 4.8 wt.-% of the component (B), based on the total weight of the aqueous disinfectant solution, can be diluted in water to prepare an aqueous disinfectant solution. In a further embodiment, from equal or more than about 4.5 wt.-% to equal or less than about 4.8 wt.-% of the component (A) and from equal or more than about 4.2 wt.-% to equal or less than about 4.8 wt.-% of the component (B), based on the total weight of the aqueous disinfectant solution, can be diluted in water to prepare an aqueous disinfectant solution.

The aqueous disinfectant solution can be very easily prepared by dispersing or dissolving the components (A) and (B) of the disinfectant composition in water. Further, the aqueous disinfectant solution needs no activation period before being usable for disinfection. Advantageously, the aqueous disinfectant solution can show a rapid microbial efficacy.

The aqueous disinfectant solution can be active against a wide range of organisms including mycobacteria, and can significantly reduce the population of bacteria, fungi, spores and viruses on a surface such as a surface of a medical instrument.

Further provided is a method for disinfecting a surface comprising the steps of providing the aqueous disinfectant solution, and contacting the surface with the aqueous disinfectant solution for an effective period of time to disinfect the surface. In an embodiment, the method is a method for disinfecting an instrument comprising the steps of providing the aqueous disinfectant solution, and contacting the instrument with the aqueous disinfectant solution for an effective period of time to disinfect the instrument.

The exposure time of surfaces or instruments being disinfected to the aqueous disinfectant solution may vary according to the intended effect. The exposure time of surfaces or instruments being disinfected to the aqueous disinfectant solution may be in a range from about 0.5 minutes to about 15 minutes, or in a range from about 5 minute to about 15 minutes. The aqueous disinfectant solution may be used at any temperature, preferably at ambient temperature. The aqueous disinfectant solution can show bactericidal activity, yeasticidal activity, virucidal activity, tuberculocidal activity, and/or sporicidal activity.

The aqueous disinfectant solution is suitable for the disinfection of surfaces, medical instruments and devices. The aqueous disinfectant solution particularly is suitable for the disinfection of medical instruments and devices. The disinfectant advantageously is compatible with delicate instruments and sensitive medical apparatus. This is particularly important with complex and sensitive devices as endoscopes, in particular flexible endoscopes.

In an embodiment, the method is a method for the manual disinfection of instruments, particularly a method for the manual disinfection of flexible endoscopes.

The advantageous combination of disinfection efficacy with material compatibility and safety for the user renders the aqueous disinfectant solution particularly suitable for the manual disinfection of flexible endoscopes.

All publications and patent applications in this specification are indicative of the level of ordinary skill in the art to which this invention pertains. The invention has been described to various specific and preferred embodiments and techniques. However, it should be understood that many variations and modifications may be made while remaining within the spirit and scope of the invention.

For a more complete understanding of the invention, the following examples are given to illustrate some embodiments. These examples and experiments are to be understood as illustrative and not limiting.

Example 1

Preparation of a Disinfectant Composition

For preparing the peracetic acid-generating component (A), 12.75 g acetic acid 80% (Celanese), 1 g hydroxyethylidene diphosphonic acid 60% (Rhodia), and 47.8 g hydrogen peroxide 60% were mixed in 38.45 g deionized water.

For preparing the stabilizer component (B), 9.9 g sodium hydroxide 50% (Dow Chemicals) and 0.1 g N,N-bis(carboxymethyl)-L-glutamic acid tetrasodium salt (AKZO), methylglycine diacetic acid (BASF), or trisodium nitrilotriacetate, respectively, were mixed in 94.95 g deionized water.

The peracetic acid-generating component (A) and the stabilizer component (B) were stored at ambient temperature of 23° C. until use.

Example 2

Preparation of an Aqueous Disinfectant Solution

For preparing the aqueous disinfectant solution, 450 ml peracetic acid-generating component (A) as prepared according to example 1 were added to 9.13 L of deionized water and stirred. To this solution 420 ml of the stabilizer component (B) as prepared according to example 1 were added and stirred.

Example 3

Determination of the Shelf-Life of the Aqueous Disinfectant Solution

TABLE 1

| Peracetic acid-generating component (A) of the invention | | | |
|---|---|---|---|
| Substance | Example 1 | Example 2 | Example 3 |
| acetic acid [wt. - %] | 10.2 | 10.2 | 10.2 |
| hydroxyethylidene diphosphonic acid [wt. - %] | 0.6 | 0.6 | 0.6 |
| hydrogen peroxide [wt. - %] | 28.698 | 28.698 | 28.698 |
| water, deionised [wt. - %] | ad 100 | ad 100 | ad 100 |

TABLE 2

| stabilizer component (B) of the invention | | | |
|---|---|---|---|
| Substance | Example 1 | Example 2 | Example 3 |
| sodium hydroxide [wt. - %] | 4.95 | 4.95 | 4.95 |
| N,N-bis(carboxymethyl)-L-glutamic acid tetrasodium salt [wt. - %] | 0.1 | — | — |

TABLE 2-continued stabilizer component (B) of the invention

| Substance | Example 1 | Example 2 | Example 3 |
|---|---|---|---|
| methylglycine diacetic acid [wt. - %] | — | 0.1 | — |
| trisodium nitrilotriacetate [wt. - %] | — | — | 0.1 |
| ethylenediaminetetraacetic acid (EDTA) tetra sodium salt [wt. - %] | — | — | — |
| hydroxyethylidene diphosphonic acid [wt. - %] | — | — | — |
| Aqua Purificata Ph. Eur. [wt. - %] | 94.95 | 94.95 | 94.95 |

TABLE 3

Peracetic acid-generating component (A) for comparison

| Substance | comparative example 4 | comparative example 5 |
|---|---|---|
| acetic acid [wt. - %] | 10.2 | 10.2 |
| hydroxyethylidene diphosphonic acid [wt. - %] | 0.6 | 0.6 |
| hydrogen peroxide [wt. - %] | 28.698 | 28.698 |
| water, deionised [wt. - %] | Add. 100 | Add. 100 |

TABLE 4 stabilizer component (B) for comparison

| Substance | comparative Example 4 | comparative Example 5 |
|---|---|---|
| sodium hydroxide [wt. - %] | 4.95 | 4.95 |
| N,N-bis(carboxymethyl)-L-glutamic acid tetrasodium salt [wt. - %] | — | — |
| methylglycine diacetic acid [wt. - %] | — | — |
| trisodium nitrilotriacetate [wt. - %] | — | — |
| ethylenediaminetetraacetic acid (EDTA) tetra sodium salt [wt. - %] | 0.1 | — |
| hydroxyethylidene diphosphonic acid [wt. - %] | — | 5.0 |
| Aqua Purificata Ph. Eur. [wt. - %] | 94.95 | 90.05 |

In table 1 and 2 examples 1, 2, and 3 comprise stabilizer components (B) according to the invention containing 0.1% w/w N,N-bis(carboxymethyl)-L-glutamic acid tetrasodium salt, methylglycine diacetic acid, or trisodium nitrilotriacetate, respectively, as chelating agent. Comparative examples 4 and 5 contain 0.1% w/w ethylenediaminetetraacetic acid (EDTA) tetra sodium salt or 5% w/w hydroxyethylidene diphosphonic acid, respectively, as chelating agent.

The peracetic acid-generating components (A) and the stabilizer components (B) were prepared as described in example 1. For starting the experiment, for each example an aqueous solution was prepared by diluting 450 ml of the respective component (A) and 420 ml of the respective component (B) in deionised water.

The aqueous solutions were stored in a sealed plastic container (2 L Sekusept Instrument basin, Firma Ecolab) at 23° C. for 15 days. At intervals, probes of the solution were removed and the concentration of peracetic acid was measured. The determination of the peracetic acid was measured by iodometric titration at 0-4° C.

The following table 5 shows the results of the determination of peracetic acid concentration at intervals over 15 days:

TABLE 5 peracetic acid concentration [ppm] of the aqueous disinfectant solutions over 15 days:

| Time [days] | 0 | 1 | 4 | 6 | 7 | 8 | 9 | 15 |
|---|---|---|---|---|---|---|---|---|
| Example 1 | 2346 | 2202 | 1856 | 1793 | 1682 | 1636 | 1566 | 1075 |
| Example 2 | 2354 | 2191 | 1898 | 1794 | 1702 | 1679 | 1653 | 1208 |
| Example 3 | 2330 | 2180 | 1864 | 1790 | 1678 | 1651 | 1587 | 1180 |
| Comparative Example 4 | 2326 | 2158 | 1713 | 1584 | 1525 | 1325 | 1211 | 654 |
| Comparative Example 5 | 2554 | 2126 | 1400 | 1198 | 1140 | 942 | 817 | 366 |

It can be seen in table 5 that for the aqueous disinfectant solutions containing N,Nbis(carboxymethyl)-L-glutamic acid tetrasodium salt, methylglycine diacetic acid or trisodium nitrilotriacetate as chelating agent, the peracetic acid concentration in solution was kept at a level above 1000 ppm for 15 days of storage, while for the comparative examples the peracetic acid concentration in solution fell below 1000 ppm after 8 or 12 days of storage, respectively.

This shows that a superior stabilisation of peracetic acid was achieved by N,Nbis(carboxymethyl)-L-glutamic acid tetrasodium salt, methylglycine diacetic acid or trisodium nitrilotriacetate as chelating agent at a concentration of 0.1% w/w in the component (B) compared to ethylenediaminetetraacetic acid (EDTA) tetra sodium salt at a concentration of 0.1 wt.-% or hydroxyethylidene diphosphonic acid at a concentration of 5 wt.-%. Further, this experiment shows that the shelf life of the aqueous disinfectant use solution was prolonged to more than 14 days.

Example 4

Screening of Different Concentrations of the Chelating Agent N,N-Bis(Carboxymethyl)-L-glutamic Acid Tetrasodium Salt For comparing different concentrations of the chelating agent N,N-bis(carboxymethyl)-L-glutamic acid tetrasodium salt (GLDA), different stabilizer components (B), comprising 4.95 wt.-% sodium hydroxide and 0.05 wt.-%, 0.1 wt.-% or 0.5 wt.-% N,N-bis(carboxymethyl)-L-glutamic acid tetrasodium salt, respectively, were prepared in purified water (Aqua Purificata Ph. Eur.).

The peracetic acid-generating component (A) and the stabilizer component (B) were prepared as described in example 1, wherein the stabilizer component (B) differed in that the stabilizer component (B) comprised different amounts of N,N-bis(carboxymethyl)-L-glutamic acid tetrasodium salt (GLDA). For starting the experiment, aqueous solutions were prepared by diluting 450 ml of the component (A) and 420 ml of the respective component (B) in deionised water. The aqueous disinfectant solutions were stored in a sealed plastic container at 23° C. for 15 days. At intervals, probes of the solution were removed and the concentration of peracetic acid was measured as described in example 3.

The following table 6 shows the results of the determination of peracetic acid concentration at intervals over 15 days:

TABLE 6

| GLDA concen- tration in component (B) | peracetic acid concentration [ppm] of the aqueous disinfectant solutions over 15 days: Time [days] | | | | | | | |
|---|---|---|---|---|---|---|---|---|
| | 0 | 1 | 4 | 6 | 7 | 8 | 9 | 15 |
| 0.05 wt.-% | 2314 | 2220 | 1847 | 1753 | 1653 | 1563 | 1466 | 829 |
| 0.1 wt.-% | 2346 | 2202 | 1856 | 1793 | 1682 | 1636 | 1566 | 1075 |
| 0.5 wt.-% | 2408 | 2113 | 1821 | 1718 | 1682 | 1625 | 1512 | 1016 |

This experiment shows that the shelf life of the aqueous disinfectant use solution was prolonged to about 14 days when the component (B) comprised 0.05 wt.-%, 0.1 wt.-% or 0.5 wt.-% N,N-bis(carboxymethyl)-L-glutamic acid tetrasodium salt (GLDA), wherein the best stabilisation was achieved using N,N-bis(carboxymethyl)-L-glutamic acid tetrasodium salt (GLDA) at a concentration of 0.1 wt.-% in the stabilizer component (B).

In summary, the above experiments show that the disinfectant composition according to the invention provide an improved shelf life of the aqueous disinfectant use solution.

What is claimed is:

1. An aqueous disinfectant solution obtainable by diluting a two-component disinfectant composition, wherein the disinfectant composition comprises:
   (A) a peracetic acid-generating component consisting of acetic acid, hydrogen peroxide, an organic phosphonic acid, and water; and
   (B) a stabilizer component comprising from about 3 wt.-% to about 10 wt.-% of sodium hydroxide; and a chelating agent, wherein the chelating agent is N,N-bis(carboxymethyl)L-glutamic acid, methylglycine diacetic acid, nitrilotriacetic acid, an alkali metal salt thereof, or a mixture thereof,
   wherein the peracetic acid in the aqueous disinfectant solution is stable for 7 days or more.

2. The aqueous disinfectant composition according to claim 1, wherein the stabilizer component (B) comprises from equal or more than about 0.05 wt.-% to equal or less than about 3 wt.-% of the chelating agent.

3. The aqueous disinfectant composition according to claim 1, wherein the chelating agent is N,N-bis(carboxymethyl)-L-glutamic acid tetrasodium salt.

4. The aqueous disinfectant composition according to claim 1, wherein the stabilizer component (B) comprises about 5 wt.-% of sodium hydroxide.

5. The aqueous disinfectant composition according to claim 1, wherein the acetic acid of the peractic acid-generating component is from equal or more than about 5 wt.-% to equal or less than about 20 wt.-% of acetic acid.

6. The aqueous disinfectant composition according to claim 1, wherein the hydrogen peroxide of the peracetic acid-generating component (A) is from equal or more than about 20 wt.-% to equal or less than about 40 wt.-% of hydrogen peroxide.

7. The aqueous disinfectant composition according to claim 1, wherein the organic phosphonic acid is hydroxyethylidene diphosphonic acid and diethylenetriamine penta (methylene phosphonic acid).

8. The aqueous disinfectant composition according to claim 1, wherein the organic phosphonic acid of the peracetic acid-generating component (A) is from equal or more than about 0.1 wt.-% to equal or less than about 5 wt.-% of the organic phosphonic acid.

9. The aqueous disinfectant solution composition according to claim 1, wherein the disinfectant solution has a pH value in the range from equal or more than about 3 to equal or less than about 7.

10. The aqueous disinfectant solution composition according to claim 1, wherein the aqueous disinfectant solution comprises from equal or more than about 1000 ppm to equal or less than about 3000 ppm, based on the total weight of the disinfectant solution, of peracetic acid, for at least 7 days.

11. A method for disinfecting a surface comprising:
   providing the aqueous disinfectant composition of claim 1;
   and
   contacting the surface with the aqueous disinfectant solution for an effective period of time to disinfect the surface.

12. The method according to claim 11, wherein the method is a method for the manual disinfection of instruments, wherein the instruments include flexible endoscopes.

13. The method according to claim 11, wherein the diluting of the disinfectant composition generates an aqueous disinfectant solution comprising equal or more than about 3 wt.-% to equal or less than about 6 wt.-% of the component (A) and from equal or more than about 3 wt.-% to equal or less than about 6 wt.-% of the component (B), based on the total weight of the aqueous disinfectant solution, in water.

* * * * *

UNITED STATES PATENT AND TRADEMARK OFFICE
CERTIFICATE OF CORRECTION

PATENT NO. : 11,140,896 B2
APPLICATION NO. : 16/801607
DATED : October 12, 2021
INVENTOR(S) : Geret et al.

Page 1 of 2

It is certified that error appears in the above-identified patent and that said Letters Patent is hereby corrected as shown below:

On the Title Page

Item (56) References Cited, under OTHER PUBLICATIONS, Lines 10-11:
DELETE: "Wissenschaffliche"
INSERT: --Wissenschaftliche--
DELETE: "Restock,"
INSERT: --Rostock,--

In the Claims

In Claim 2, at Column 11, Line 39:
DELETE: "The aqueous disinfectant composition"
INSERT: --The aqueous disinfectant solution composition--

In Claim 3, at Column 11, Line 43:
DELETE: "The aqueous disinfectant composition"
INSERT: --The aqueous disinfectant solution composition--

In Claim 4, at Column 11, Line 46:
DELETE: "The aqueous disinfectant composition"
INSERT: --The aqueous disinfectant solution composition--

In Claim 5, at Column 11, Line 49:
DELETE: "The aqueous disinfectant composition"
INSERT: --The aqueous disinfectant solution composition--

In Claim 5, at Column 11, Line 50:
DELETE: "peractic"
INSERT: --peracetic--

Signed and Sealed this
Twenty-fourth Day of May, 2022

Katherine Kelly Vidal
*Director of the United States Patent and Trademark Office*

CERTIFICATE OF CORRECTION (continued)
U.S. Pat. No. 11,140,896 B2

<u>In Claim 6, at Column 12, Line 4:</u>
DELETE: "The aqueous disinfectant composition"
INSERT: --The aqueous disinfectant solution composition--

<u>In Claim 7, at Column 12, Line 9:</u>
DELETE: "The aqueous disinfectant composition"
INSERT: --The aqueous disinfectant solution composition--

<u>In Claim 8, at Column 12, Line 13:</u>
DELETE: "The aqueous disinfectant composition"
INSERT: --The aqueous disinfectant solution composition--